(12) United States Patent
Martin et al.

(10) Patent No.: US 6,664,269 B2
(45) Date of Patent: Dec. 16, 2003

(54) ISOQUINOLINONE DERIVATIVES

(75) Inventors: Niall Morrison Barr Martin, Cambridge (GB); Graeme Cameron Murray Smith, Cambridge (GB); Charles Richard White, Cumbria (GB); Roger Frank Newton, Cornwall (GB); Diana Gillian Douglas, Cornwall (GB); Penny Jane Eversley, Cornwall (GB); Alan John Whittle, Cornwall (GB)

(73) Assignees: Maybridge plc (GB); KuDOS Pharmaceuticals Limited (GB)

( * ) Notice: Subject to any disclaimer, the term of this patent is extended or adjusted under 35 U.S.C. 154(b) by 0 days.

(21) Appl. No.: 10/135,247

(22) Filed: Apr. 30, 2002

(65) Prior Publication Data
US 2003/0008896 A1 Jan. 9, 2003

Related U.S. Application Data
(60) Provisional application No. 60/289,631, filed on May 8, 2001, and provisional application No. 60/345,274, filed on Jan. 3, 2002.

(51) Int. Cl.[7] .................. A61K 31/47; C07D 217/12
(52) U.S. Cl. ......................... 514/309; 546/141
(58) Field of Search ..................... 546/141; 514/309

(56) References Cited

U.S. PATENT DOCUMENTS

| | | |
|---|---|---|
| 2,612,503 A | 9/1952 | Ullyot |
| 4,897,391 A | 1/1990 | Friary |
| 5,032,617 A | 7/1991 | Lee et al. |
| 5,041,653 A | 8/1991 | Lee et al. |
| 5,215,738 A | 6/1993 | Lee et al. |
| 5,874,444 A | 2/1999 | West |
| 6,197,785 B1 | 3/2001 | Jackson et al. |
| 6,262,068 B1 | 7/2001 | Atwal et al. |

FOREIGN PATENT DOCUMENTS

| | | |
|---|---|---|
| DE | 21 43 745 | 3/1973 |
| DE | 287 032 A5 | 2/1991 |
| EP | 0 030 861 | 6/1981 |
| EP | 0 269 968 | 6/1988 |
| EP | 0 355 750 | 2/1990 |
| EP | 0 389 955 | 10/1990 |
| EP | 0 502 575 | 9/1992 |
| GB | 721 286 | 1/1955 |
| JP | 54 156526 | 12/1979 |
| JP | 58 164577 | 9/1983 |
| WO | WO 91/18591 | 12/1991 |
| WO | WO 93/14086 | 7/1993 |
| WO | WO 98/51308 | 11/1998 |
| WO | WO 99/08680 | 2/1999 |
| WO | WO 99/11624 | 3/1999 |
| WO | WO 99/11645 | 3/1999 |
| WO | WO 99/11649 | 3/1999 |
| WO | WO 00/42040 | 7/2000 |
| WO | WO 01/16137 A1 | 3/2001 |
| WO | WO 02/44157 | 6/2002 |

OTHER PUBLICATIONS

Belgaonkar, et al., "Isocoumarins: Part XIV—Synthesis of 3–Benzylisocoumarins and 3–Benzyl–I (2H)–isoquinolones", Indian J. Chemistry, 13(4): 336–338 (1975).
Dusemund, et al., "Einfache Synthese von Isochinol[2,3–c] [2,3]benzoxazepinon und –[2,3]benzodiazepinonen sowie ihrer Vorstufen", Arch. Pharm., 321(1) 41–44 (1988).
Modi, et al., "Isoquinolones—An Elegant Synthesis for 3–Acetyl and 3–Benzoyl–Isoquinolones" Curr. Sci., 48(13): 580–581 (1979).
Wu, et al., "A Direct Anionic Cyclization of 2–Alkynylbenzonitrile to 3–Substituted–1(2H)–isoquinolones and 3–Benzylideneisoindol–2–ones Initiated by Methoxide Addition" Tetrahedron, 55(46): 13193–13200 (1999).
Althause, F.R. and Richter, C., (1987) ADP–Ribosylation of Proteins; Enzymology and Biological Significance, Springer–Verley, Berlin.
Basanick, et al., J. Biol. Chem. (1992) 267:1569–1575.
Ben–Hur et al., British J. of Cancer (1984) 49(Suppl. VI):39–42.
Berge, et al., J. Pharm. Sci. (1977) 66:1–19.
Berger, N.A., Radiation Research (1985) 101:4–14.
Beugelmans & Bois–Choussy, Synthesis, (1982) 9:729–731.
Burkhart, et al., Horm. Metab. Res., (1999) 31:641–644.
Burzio, et al., Proc. Soc. Exp. Biol. Med. (1975) 149:933–938.
Cantoni, et al., Biochim. Biophys. Acta. (1989) 1014:1–7.
Cosi, et al., J. Neurosci. Res. (1994) 39:38–46.
d'Adda di Fagagna, et al., Nature Gen. (1999) 23(1):76–80.
D'Amours, et al., Biochem. J. (1999) 342:249–268.
Dutkscz, et al., Nature (1980) 283:593–596.
Elliott, I.W. and Takekoshi, Y., J. Heterocyclic Chem. (1976) 13:597.
Gäken, et al., J. Virology (1996) 70(6):3992–4000.
Glushkov, U.A. and Shkyaev, Y.U., J. Heterocyclic Chem. (2001) 37(6):663–687.
Hirai, et al., Cancer Res. (1983) 43:3441–3446.
Kimura, et al., Chem Pharm. Bull. (1983) 31(4):1277–1282.
Liaudet, et al., PNAS, USA (2000) 97(3):10203–10208.
Menissier de Murcia, et al., PNAS, USA (1997) 94:7303–7307.
Miwa, et al., Arch. Biochem. Biophys. (1977) 181:313–321.
Perkins, et al., Cancer Research (2001) 61:4175–4183.
Rama, et al., Indian J. Chem. Section B (1998) 37:1021.
Rattan and Clark, Biochem. Biophys. Res. Comm. (1994) 201(2):665–672.
Rhun, et al., Biochem. Biophys. Res. Comm. (1998) 245:1–10.

(List continued on next page.)

Primary Examiner—Zinna Northington Davis
(74) Attorney, Agent, or Firm—Michael Best & Friedrich, LLP; Grady J. Frenchick; Charles L. Yager

(57) ABSTRACT

Derivatives of isoquinolinone and dihydroisoquinolinone, and related compounds, and their use as pharmaceuticals in the treatment of a disease by inhibition of the enzyme poly(ADP-ribose)polymerase ("PARP") are disclosed.

10 Claims, No Drawings

OTHER PUBLICATIONS

Said, et al., *PNAS, USA* (1996) 93:4688–4692.
Schlicker, et al., *Int. J. Radiat. Biol.* (1999) 75:91–100.
Skehan, P., *J. Natl. Cancer Inst.* (1990) 82:1107–1112.
Suto, et al., *Anti–Cancer Drug Design* (1991) 7:107–117.
Szabo, et al., *J. Clin. Invest.* (1997) 100:723–735.

Wang, et al., *Genes Dev.* (1995) 9:509–520.

Watson, et al., *Bioorganic & Medicinal Chemistry* (1998) 6:721–734.

Zhang, et al., *Portland Press Proc.* (1999) 15 (Biology of Nitric Oxide, Part 6) 125.

ISOQUINOLINONE DERIVATIVES

This application claims priority to U.S. Provisional Application No. 60/289,631, filed May 8, 2001, and U.S. Provisional Application No. 60/345,274, filed Jan. 3, 2002, the contents of which are incorporated herein by reference in their entirety.

The present invention relates to isoquinolinone derivatives, and their use as pharmaceuticals. In particular, the present invention relates to the use of these compounds to inhibit the activity of the enzyme poly (ADP-ribose) polymerase, also known as poly(ADP-ribose)synthase and poly ADP-ribosyltransferase, and commonly referred to as PARP.

The mammalian enzyme PARP (a 113-kDa multidomain protein) has been implicated in the signalling of DNA damage through its ability to recognize and rapidly bind to DNA single or double strand breaks (D'Amours et al, 1999, Biochem. J. 342: 249–268).

Several observations have led to the conclusion that PARP participates in a variety of DNA-related functions including gene amplification, cell division, differentiation, apoptosis, DNA base excision repair and also effects on telomere length and chromosome stability (d'Adda di Fagagna et al, 1999, Nature Gen., 23(1): 76–80).

Studies on the mechanism by which PARP modulates DNA repair and other processes has identified its importance in the formation of poly (ADP-ribose) chains within the cellular nucleus (Althaus, F. R. and Richter, C., 1987, ADP-Ribosylation of Proteins: Enzymology and Biological Significance, Springer-Verlag, Berlin). The DNA-bound, activated PARP utilizes NAD to synthesize poly (ADP-ribose) on a variety of nuclear target proteins, including topoisomerase, histones and PARP itself (Rhun et al, 1998, Biochem. Biophys. Res. Commun., 245: 1–10)

Poly (ADP-ribosyl)ation has also been associated with malignant transformation. For example, PARP activity is higher in the isolated nuclei of SV40-transformed fibroblasts, while both leukemic cells and colon cancer cells show higher enzyme activity than the equivalent normal leukocytes and colon mucosa (Miwa et al, 1977, Arch. Biochem. Biophys. 181: 313–321; Burzio et al, 1975, Proc. Soc. Exp. Bioi. Med. 149: 933–938; and Hirai et al, 1983, Cancer Res. 43: 3441–3446).

A number of low-molecular-weight inhibitors of PARP have been used to elucidate the functional role of poly (ADP-ribosyl)ation in DNA repair. In cells treated with alkylating agents, the inhibition of PARP leads to a marked increase in DNA-strand breakage and cell killing (Durkacz et al, 1980, Nature 283: 593–596; Berger, N. A., 1985, Radiation Research, 101: 4–14).

Subsequently, such inhibitors have been shown to enhance the effects of radiation response by suppressing the repair of potentially lethal damage (Ben-Hur et al, 1984, British Journal of Cancer, 49 (Suppl. VI): 34–42; Schlicker et al, 1999, Int. J. Radiat. Bioi., 75: 91–100). PARP inhibitors have been reported to be effective in radio sensitising hypoxic tumour cells (U.S. Pat. Nos. 5,032,617; 5,215,738 and 5,041,653).

Furthermore, PARP knockout (PARP −/−) animals exhibit genomic instability in response to alkylating agents and γ-irradiation (Wang et al, 1995, Genes Dev., 9: 509–520; Menissier de Murcia et al, 1997, Proc. Natl. Acad. Sci. USA, 94: 7303–7307).

A role for PARP has also been demonstrated in certain vascular diseases, septic shock, ischaemic injury and neurotoxicity (Cantoni et al, 1989, Biochim. Biophys. Acta, 1014: 1–7; Szabo, et al, 1997, J. Clin. Invest., 100: 723–735). Oxygen radical DNA damage that leads to strand breaks in DNA, which are subsequently recognised by PARP, is a major contributing factor to such disease states as shown by PARP inhibitor studies (Cosi et al, 1994, J. Neurosci. Res., 39: 38–46; Said et al, 1996, Proc. Natl. Acad. Sci. U.S.A., 93: 4688–4692). More recently, PARP has been demonstrated to play a role in the pathogenesis of haemorrhagic shock (Liaudet et al, 2000, Proc. Natl. Acad. Sci. U.S.A., 97(3): 10203–10208).

It has also been demonstrated that efficient retroviral infection of mammalian cells is blocked by the inhibition of PARP activity. Such inhibition of recombinant retroviral vector infections was shown to occur in various different cell types (Gaken et al, 1996, J. Virology, 70(6): 3992–4000). Inhibitors of PARP have thus been developed for the use in anti-viral therapies and in cancer treatment (WO91/18591)

Moreover, PARP inhibition has been speculated to delay the onset of aging characteristics in human fibroblasts (Rattan and Clark, 1994, Biochem. Biophys. Res. Comm., 201 (2): 665–672). This may be related to the role that PARP plays in controlling telomere function (d'Adda di Fagagna et al, 1999, Nature Gen., 23(1): 76–80).

EP 0 355 750 discloses classes of 5-substituted isoquinolinones and dihydroisoquinolinones as PARP inhibitors. Exemplified substituents on the nitrogen containing ring, at the 3 and/or 4 position, include methyl, phenyl, bromo or amino.

WO 99/11624 discloses a number of PARP inhibitors, amongst which are some isoquinolinone derivatives.

The present inventors have now discovered that further derivatives of isoquinolinone and dihydroisoquinolinone and related compounds act as PARP inhibitors.

Accordingly, the first aspect of the present invention provides a method of treatment of a disease of the human or animal body mediated by PARP comprising administering to such a subject a therapeutically effective amount of a compound of formula:

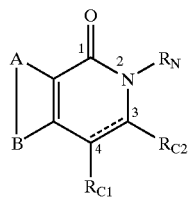

and isomers, salts, solvates, chemically protected forms, and prodrugs thereof, wherein:

A and B together represent an optionally substituted, fused aromatic ring;

the dotted line between the 3 and 4 positions indicates the optional presence of a double bond;

at least one of $R_{C1}$ and $R_{C2}$ is independently represented by -L-$R_L$, and if one of $R_{C1}$ and $R_{C2}$ is not represented by -L-$R_L$, then that group is H, where L is of formula:

$$-(CH_2)_{n1}-Q_{n2}-(CH_2)_{n3}-$$

wherein $n_1$, $n_2$ and $n_3$ are each selected from 0, 1, 2 and 3, the sum of $n_1$, $n_2$ and $n_3$ is 1, 2 or 3 and each Q (if $n_2$ is greater than 1) is selected from O, S, $NR_3$, C(=O), or -$cR_1R_2$—, where $R_1$ and $R_2$ are independently selected from hydrogen, halogen or optionally substituted $C_{1-7}$ alkyl, or may together with the carbon atom to which they are attached form a $C_{3-7}$ cyclic alkyl group, which may be saturated (a $C_{3-7}$ cycloalkyl group) or unsaturated (a $C_{3-7}$ cycloalkenyl group), or one of $R_1$ and $R_2$ may be attached to an atom in $R_L$ to form an unsaturated $C_{3-7}$ cycloalkenyl group which comprises the carbon atoms to which $R_1$ and $R_2$ are attached in Q, —$(CH_2)_{n3}$— (if present) and part of $R_L$, and where $R_3$ is selected from H or $C_{1-7}$ alkyl; and $R_L$ is selected from optionally substituted $C_{3-20}$ heterocyclyl, $C_{5-20}$ aryl and carbonyl; and $R_N$ is selected from hydrogen, optionally substituted $C_{1-7}$ alkyl, $C_{3-20}$ heterocyclyl, $C_{5-20}$ aryl, hydroxy, ether, nitro, amino, thioether, sulfoxide and sulfone.

A second aspect of the present invention relates to a compound of the formula:

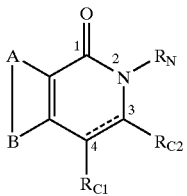

or an isomer, salt, solvate, chemically protected form, and prodrug thereof, wherein:

A and B together represent an optionally substituted, fused aromatic ring;

the dotted line between the 3 and 4 positions indicates the optional presence of a double bond;

one of $R_{C1}$ and $R_{C2}$ is —$CH_2$—$R_L$, and the other of $R_{C1}$ and $R_{C2}$ is H;

$R_L$ is optionally substituted phenyl; and $R_N$ is hydrogen.

A third aspect of the present invention relates to a pharmaceutical composition comprising a compound of the second aspect and a pharmaceutically acceptable carrier or diluent.

Further aspects of the invention provide for a method of treatment as described in the first aspect of the invention, wherein the disease mediated by PARP is: vascular disease; septic shock; ischaemic injury; neurotoxicity; haemorraghic shock; or viral infection.

A further aspect of the invention provides a method of cancer therapy for the human or animal body comprising administering to such a subject a therapeutically effective amount of a compound as described in the first aspect in combination with chemotherapy or radiation therapy.

Another further aspect of the invention provides a method of potentiating tumour cells for treatment with ionising radiation or chemotherapeutic agents comprising administering to said cells a compound as described in the first aspect of the invention. such a method may be practised in vivo or in vitro.

It is preferred that when a compound is administered it is done so in the form of a pharmaceutical composition.

Definitions

The term "aromatic ring" is used herein in the conventional sense to refer to a cyclic aromatic structure, that is, a cyclic structure having delocalised π-electron orbitals.

The aromatic ring fused to the main core, i.e. that formed by -A-B-, may bear further fused aromatic rings (resulting in, e.g. naphthyl or anthracenyl groups). The aromatic ring(s) may comprise solely carbon atoms, or may comprise carbon atoms and one or more heteroatoms, including but not limited to, nitrogen, oxygen, and sulfur atoms. The aromatic ring(s) preferably have five or six ring atoms.

The aromatic ring(s) may optionally be substituted. If a substituent itself comprises an aryl group, this aryl group is not considered to be a part of the aryl group to which it is attached. For example, the group biphenyl is considered herein to be a phenyl group (an aryl group comprising a single aromatic ring) substituted with a phenyl group. Similarly, the group benzylphenyl is considered to be a phenyl group (an aryl group comprising a single aromatic ring) substituted with a benzyl group.

In one group of preferred embodiments, the aromatic group comprises a single aromatic ring, which has five or six ring atoms, which ring atoms are selected from carbon, nitrogen, oxygen, and sulfur, and which ring is optionally substituted. Examples of these groups include benzene, pyrazine, pyrrole, thiazole, isoxazole, and oxazole. 2-Pyrone can also be considered to be an aromatic ring, but is less preferred.

If the aromatic ring has six atoms, then preferably at least four, or even five or all, of the ring atoms are carbon. The other ring atoms are selected from nitrogen, oxygen and sulphur, with nitrogen and oxygen being preferred. Suitable groups include a ring with: no hetero atoms (benzene); one nitrogen ring atom (pyridine); two nitrogen ring atoms (pyrazine, pyrimidine and pyridazine); one oxygen ring atom (pyrone); and one oxygen and one nitrogen ring atom (oxazine).

If the aromatic ring has five ring atoms, then preferably at least three of the ring atoms are carbon. The remaining ring atoms are selected from nitrogen, oxygen and sulphur. Suitable rings include a ring with: one nitrogen ring atom (pyrrole); two nitrogen ring atoms (imidazole, pyrazole); one oxygen ring atom (furan); one sulphur ring atom (thiophene); one nitrogen and one sulphur ring atom (isothiazole or thiazole); and one nitrogen and one oxygen ring atom (isoxazole or oxazole).

The aromatic ring may bear one or more substituent groups at any available ring position. These substituents are selected from halo, nitro, hydroxy, ether, thiol, thioether, amino, $C_{1-7}$ alkyl, $C_{3-20}$ heterocyclyl and $C_{5-20}$ aryl. The aromatic ring may also bear one or more substituent groups which together form a ring. In particular these may be of formula —$(CH_2)_m$— or —O—$(CH_2)_p$—O—, where m is 2, 3, 4 or 5 and p is 1, 2 or 3.

$C_{1-7}$ alkyl: The term "$C_{1-7}$ alkyl" as used herein, pertains to a monovalent moiety obtained by removing a hydrogen atom from a $C_{1-7}$ hydrocarbon compound having from 1 to 7 carbon atoms, which may be aliphatic or alicyclic, or a combination thereof, and which may be saturated, partially unsaturated, or fully unsaturated.

Examples of (unsubstituted) saturated linear $C_{1-7}$ alkyl groups include, but are not limited to, methyl, ethyl, n-propyl, n-butyl, and n-pentyl (amyl).

Examples of (unsubstituted) saturated branched $C_{1-7}$ alkyl groups include, but are not limited to, iso-propyl, iso-butyl, sec-butyl, tert-butyl, and neo-pentyl.

Examples of saturated alicyclic (carbocyclic) $C_{1-7}$ alkyl groups (also referred to as "$C_{3-7}$ cycloalkyl" groups) include, but are not limited to, unsubstituted groups such as cyclopropyl, cyclobutyl, cyclopentyl, and cyclohexyl, as well as substituted groups (e.g. groups which comprise such groups), such as methylcyclopropyl, dimethylcyclopropyl, methylcyclobutyl, dimethylcyclobutyl, methylcyclopentyl, dimethylcyclopentyl, methylcyclohexyl, cyclopropylmethyl and cyclohexylmethyl.

Examples of (unsubstituted) unsaturated $C_{1-7}$ alkyl groups which have one or more carbon—carbon double bonds (also referred to as "$C_{2-7}$ alkenyl" groups) include, but are not limited to, ethenyl (vinyl, —CH=$CH_2$), 2-propenyl (allyl, —$CH_2$—CH=$CH_2$), isopropenyl (—C($CH_3$)=$CH_2$), butenyl, pentenyl, and hexenyl.

Examples of (unsubstituted) unsaturated $C_{1-7}$ alkyl groups which have one or more carbon—carbon triple bonds (also referred to as "$C_{2-7}$ alkynyl" groups) include, but are not limited to, ethynyl (ethinyl) and 2-propynyl (propargyl).

Examples of unsaturated alicyclic (carbocyclic) $C_{1-7}$ alkyl groups which have one or more carbon—carbon double bonds (also referred to as "$C_{3-7}$ cycloalkenyl" groups) include, but are not limited to, unsubstituted groups such as cyclopropenyl, cyclobutenyl, cyclopentenyl, and cyclohexenyl, as well as substituted groups (e.g. groups which comprise such groups) such as cyclopropenylmethyl and cyclohexenylmethyl.

$C_{3-20}$ heterocyclyl: The term "$C_{3-20}$ heterocyclyl," as used herein, pertains to a monovalent moiety obtained by removing a hydrogen atom from a ring atom of a non-aromatic $C_{3-20}$ heterocyclic compound, said compound having one ring, or two or more rings (e.g. spiro, fused, bridged), and having from 3 to 20 ring atoms, of which from 1 to 10 are ring heteroatoms, and wherein at least one of said ring(s) is a heterocyclic ring. Preferably, each ring has from 3 to 7 ring atoms, of which from 1 to 4 are ring heteroatoms. "$C_{3-20}$" denotes ring atoms, whether carbon atoms or heteroatoms.

Examples of $C_{3-20}$ heterocyclyl groups having one nitrogen ring atom include, but are not limited to, those derived from aziridine, azetidine, azetine, pyrrolidine, pyrroline, piperidine, dihydropyridine, tetrahydropyridine, and dihydropyrrole (azoline).

Examples of $C_{3-20}$ heterocyclyl groups having one oxygen ring atom include, but are not limited to, those derived from oxirane, oxetane, oxolane (tetrahydrofuran), oxole (dihydrofuran), oxane (tetrahydropyran), dihydropyran, and pyran. Examples of substituted $C_{3-20}$ heterocyclyl groups include sugars, in cyclic form, for example, furanoses and pyranoses, including, for example, ribose, lyxose, xylose, galactose, sucrose, fructose, and arabinose.

Examples of $C_{3-20}$ heterocyclyl groups having one sulfur ring atom include, but are not limited to, those derived from thiolane (tetrahydrothiophene, thiane) and tetrahydrothiopyran.

Examples of $C_{3-20}$ heterocyclyl groups having two oxygen ring atoms include, but are not limited to, those derived from dioxane, for example 1,3-dioxane and 1,4-dioxane.

Examples of $C_{3-20}$ heterocyclyl groups having two nitrogen ring atoms include, but are not limited to, those derived from diazolidine (pyrazolidine), pyrazoline, imidazolidine, imidazoline, and piperazine.

Examples of $C_{3-20}$ heterocyclyl groups having one nitrogen ring atom and one oxygen ring atom include, but are not limited to, those derived from tetrahydrooxazole, dihydrooxazole, tetrahydroisoxazole, dihydroiosoxazole, morpholine, tetrahydrooxazine, dihydrooxazine, and oxazine.

Examples of $C_{3-20}$ heterocyclyl groups having one oxygen ring atom and one sulfur ring atom include, but are not limited to, those derived from oxathiolane and oxathiane.

Examples of $C_{3-20}$ heterocyclyl groups having one nitrogen ring atom and one sulfur ring atom include, but are not limited to, those derived from thiazoline, thiazolidine, and thiomorpholine.

Other examples of $C_{3-20}$ heterocyclyl groups include, but are not limited to, oxadiazine.

If the $C_{3-20}$ heterocyclyl is substituted, the substituents are on carbon, or nitrogen (if present), atoms.

$C_{5-20}$ aryl: The term "$C_{5-20}$ aryl," as used herein, pertains to a monovalent moiety obtained by removing a hydrogen atom from an aromatic ring atom of a $C_{5-20}$ aromatic compound, said compound having one ring, or two or more rings (e.g. fused), and having from 5 to 20 ring atoms, and wherein at least one of said ring(s) is an aromatic ring. Preferably, each ring has from 5 to 7 ring atoms.

The ring atoms may be all carbon atoms, as in "carboaryl groups," in which case the group may conveniently be referred to as a "$C_{5-20}$ carboaryl" group.

Examples of $C_{5-20}$ aryl groups which do not have ring heteroatoms (i.e., $C_{5-20}$ carboaryl groups) include, but are not limited to, those derived from benzene (i.e., phenyl) ($C_6$), naphthalene ($C_{10}$), anthracene ($C_{14}$), phenanthrene ($C_{14}$), and pyrene ($C_{16}$).

Alternatively, the ring atoms may include one or more heteroatoms, including but not limited to oxygen, nitrogen, and sulfur, as in "heteroaryl groups." In this case, the group may conveniently be referred to as a "$C_{5-20}$ heteroaryl" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of $C_{5-20}$ heteroaryl groups include, but are not limited to, $C_5$ heteroaryl groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, oxatriazole, and tetrazole; and $C_6$ heteroaryl groups derived from isoxazine, pyridine (azine), pyridazine (1,2-diazine), pyrimidine (1,3-diazine; e.g. cytosine, thymine, uracil), pyrazine (1,4-diazine), and triazine.

The heteroaryl group may be bonded via a carbon or hetero ring atom.

Examples of $C_{5-20}$ heteroaryl groups which comprise fused rings, include, but are not limited to, $C_9$ heteroaryl groups derived from benzofuran, isobenzofuran, benzothiophene, indole, isoindole; $C_{10}$ heteroaryl groups derived from quinoline, isoquinoline, benzodiazine, pyridopyridine; $C_{14}$ heteroaryl groups derived from acridine and xanthene.

The above $C_{1-7}$ alkyl, $C_{3-20}$ heterocyclyl, and $C_{5-20}$ aryl groups, whether alone or part of another substituent, may themselves optionally be substituted with one or more groups selected from themselves and the additional substituents listed below Halo: —F, —Cl, —Br, and —I.

Hydroxy: —OH.

Ether: —OR, wherein R is an ether substituent, for example, a $C_{1-7}$ alkyl group (also referred to as a $C_{1-7}$alkoxy group), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

Nitro: —$NO_2$.

Cyano (nitrile, carbonitrile): —CN.

Carbonyl: a group of structure —C(=O)—, which includes acyl, carboxy, ester and amido.

Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)$CH_3$ (acetyl), —C(=O)$CH_2CH_3$ (propionyl) —C(=O)C($CH_3$)$_3$ (pivaloyl), and —C(=O)Ph (benzoyl, phenone).

Carboxy (carboxylic acid): —COOH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)

OCH$_3$, —C(=O)OCH$_2$CH$_3$, —C(=O)OC(CH$_3$)$_3$, and —C(=O)OPh.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Amino: —NR$^1$R$^2$, wherein R$^1$ and R$^2$ are independently amino substituents, for example, hydrogen, a C$_{1-7}$ alkyl group (also referred to as C$_{1-7}$ alkylamino or di-C$_{1-7}$ alkylamino), a C$_{3-20}$ heterocyclyl group, or a C$_{5-20}$ aryl group, preferably H or a C$_{1-7}$ alkyl group, or, in the case of a "cyclic" amino group, R$^1$ and R$^2$, taken together with the nitrogen atom to which they are attached, form a heterocyclic ring having from 4 to 8 ring atoms. Examples of amino groups include, but are not limited to, —NH$_2$, —NHCH$_3$, —NHCH(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, perhydrodiazepino, morpholino, and thiomorpholino. The cyclic amino groups may be substituted on their ring by any of the substituents defined here, for example carboxy, carboxylate and amido. A particular form of amino group is where one of R$^1$ and R$^2$ is a sulfone (—S(=O)$_2$R), where R is a sulfone substituent, and this group can be termed a sulfonamido group. Examples of sulfonamido groups include, but are not limited to, —NHS(=O)$_2$CH$_3$, —NHS(=O)$_2$Ph and —NHS(=O)$_2$C$_6$H$_4$F.

Acylamido (acylamino): —NR$^1$C(=O)R$^2$, wherein R$^1$ is an amide substituent, for example, hydrogen, a C$_{1-7}$ alkyl group, a C$_{3-20}$ heterocyclyl group, or a C$_{5-20}$ aryl group, preferably H or a C$_{1-7}$alkyl group, most preferably H, and R$^2$ is an acyl substituent, for example, a C$_{1-7}$ alkyl group, a C$_{3-20}$ heterocyclyl group, or a C$_{5-20}$ aryl group, preferably a C$_{1-7}$ alkyl group. Examples of acylamido groups include, but are not limited to, —NHC(=O)CH$_3$, —NHC(=O)CH$_2$CH$_3$, and —NHC(=O)Ph. One particular form of acylamido group is where R$^2$ is an amino group (—NR$^3$R$^4$), where R$^3$ and R$^4$ are independently amino substituents, and this group can be termed an ureido group. Examples of ureido groups include, but are not limited to —NHC(=O)NHCH$_3$, —NHC(=O)NHCH$_2$CH$_3$, and —NHC(=O)NHPh.

Acyloxy (reverse ester): —OC(=O)R, wherein R is an acyloxy substituent, for example, a C$_{1-7}$ alkyl group, a C$_{3-20}$ heterocyclyl group, or a C$_{5-20}$ aryl group, preferably a C$_{1-7}$ alkyl group. Example of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, —OC(=O)CH$_4$F, and —OC(=O)CH$_2$Ph.

Thiol: —SH.

Thioether (sulfide): —SR, wherein R is a thioether substituent, for example, a C$_{1-7}$ alkyl group (also referred to as a C$_{1-7}$ alkylthio group), a C$_{3-20}$ heterocyclyl group, or a C$_{5-20}$ aryl group, preferably a C$_{1-7}$ alkyl group. Examples of C$_{1-7}$ alkylthio groups include, but are not limited to, —SCH$_3$ and —SCH$_2$CH$_3$.

Sulfoxide (sulfinyl): —S(=O)R, wherein R is a sulfoxide substituent, for example, a C$_{1-7}$ alkyl group, a C$_{3-20}$ heterocyclyl group, or a C$_{5-20}$ aryl group, preferably a C$_{1-7}$ alkyl group. Examples of sulfoxide groups include, but are not limited to, —S(=O)CH$_3$ and —S(=O)CH$_2$CH$_3$.

Sulfone (sulfonyl): —S(=O)$_2$R, wherein R is a sulfone substituent, for example, a C$_{1-7}$ alkyl group, a C$_{3-20}$ heterocyclyl group, or a C$_{5-20}$ aryl group, preferably a C$_{1-7}$ alkyl group. Examples of sulfone groups include, but are not limited to, —S(=O)$_2$CH$_3$ (methanesulfonyl, mesyl), —S(=O)$_2$CF$_3$, —S(=O)$_2$CH$_2$CH$_3$, and 4-methylphenylsulfonyl (tosyl).

As mentioned above, the groups that form the above listed substituent groups, e.g. C$_{1-7}$ alkyl, C$_{3-20}$ heterocyclyl and C$_{5-20}$ aryl, may themselves be substituted. Thus, the above definitions cover substituent groups which are substituted.

Substituents Form a Ring

It is possible that a substituent on a ring which forms part of R$_{C1}$ and a substituent on the fused aromatic ring (represented by -A-B-), may together form an intra ring link, thus forming a further cyclic structure in the compound.

The substituent on the aromatic ring that forms the intra ring link is preferably on the atom adjacent the central moiety (i.e. at the α-position).

The substituent on R$_{C1}$ that forms the intra ring link is preferably on the atom which is one atom away from the atom which is bound to the central moiety.

The link between the two rings may be a single bond, or may be of the formula:

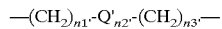

wherein n1', n2' and n3' are each selected from 0, 1, 2 and 3 and the sum of n1', n2' and n3' is less than or equal to 3. Each Q' (if n2' is greater than 1) is selected from O, S, NR'$_3$, C(=O), or —CR'$_1$R'$_2$—, where R'$_1$ and R'$_2$ are independently selected from hydrogen, halogen or optionally substituted C$_{1-7}$ alkyl, or may together with the carbon atom to which they are attached form a C$_{3-7}$ cyclic alkyl group, which may be saturated (a C$_{3-7}$ cycloalkyl group) or unsaturated (a C$_{3-7}$ cycloalkenyl group), and where R'$_3$ is selected from H or C$_{1-7}$ alkyl.

Further Preferences

It is preferred that there is a double bond present between the third and fourth positions of the compound.

It is also preferred that only one of R$_{C1}$ and R$_{C2}$ is represented by -L-R$_L$, and the other of R$_{C1}$ and R$_{C2}$ is H. The preferences for L and R$_L$ expressed below may be different for R$_{C1}$ and R$_{C2}$.

The fused aromatic ring(s) represented by -A-B- preferably consist of solely carbon ring atoms, and thus may be benzene, naphthalene, and is more preferably benzene. As described above, these rings may be substituted, but in some embodiments are preferably unsubstituted.

R$_N$ is preferably selected from hydrogen, and C$_{1-7}$ alkyl, which may be substituted or unsubstituted. In one embodiment, R$_N$ is preferably C$_{1-3}$ alkyl, which may be substituted, for example by a C$_{5-20}$ heterocyclic group. Suitable such groups include cyclic amino groups such as piperidino or morpholino. In another embodiment, R$_N$ is preferably H.

In L, it is preferred that each Q (if n2 is greater than 1) is selected from O, S, NH or C(=O).

L is preferably of formula:
—(CH$_2$)$_{n1}$-Q$_{n2}$-, where n1 is selected from 0, 1, 2 and 3 and n2 is selected from 0 and 1 (where the sum of n1 and n2 is 1, 2 or 3), and more preferably n1 is 1 or 2. The more preferred options for L are —CH$_2$— or —C$_2$H$_4$—, with —C$_2$H$_4$— being the most preferred for R$_{C2}$ and —CH$_2$— being the most preferred for R$_{C1}$.

If Q in L is —CR$_1$R$_2$—, then n2 is preferably 1. In one embodiment, R$_1$ is optionally substituted C$_{1-7}$ alkyl and R$_2$ is hydrogen. R$_1$ is more preferably optionally substituted $C_{1-4}$ alkyl, and most preferably unsubstituted $C_{1-4}$ alkyl. In another embodiment, $R_1$ and $R_2$, together with the carbon atom to which they are attached, form a saturated $C_{3-7}$ cyclic alkyl group, more preferably a $C_{5-7}$ cyclic alkyl group. In a further embodiment, $R_1$ is attached to an atom in $R_L$ to form an unsaturated $C_{3-7}$ cycloalkenyl group, more preferably a $C_{5-7}$ cycloalkenyl group, which comprises the carbon atoms to which $R_1$ and $R_2$ are attached in Q, —$(CH_2)_{n3}$— (if present) and part of $R_L$, and $R_2$ is hydrogen.

$R_L$ is preferably $C_{5-20}$ aryl, and more preferably a benzene ring, naphthalene, pyridine, 1,3-benzodioxole or furan.

When $R_L$ is a benzene ring, it is preferably substituted. The one or more substituents may be selected from: $C_{1-7}$ alkyl, more preferably methyl, $CF_3$; $C_{5-20}$ aryl; $C_{3-20}$ heterocyclyl; halo, more preferably fluoro; hydroxy; ether, more preferably methoxy, phenoxy, benzyloxy, and cyclopentoxy; nitro; cyano; carbonyl groups, such as carboxy, ester and amido; amino (including sulfonamido), more preferably —$NH_2$, —NHPh, and cycloamino groups, such as morpholino; acylamido, including ureido groups, where the acyl or amino substituent is preferably phenyl, which itself is optionally fluorinated; acyloxy; thiol; thioether; sulfoxide; sulfone.

In one group of embodiments, fluoro is particularly preferred as a substituent, along with substituents containing a phenyl, or fluorinated phenyl, component.

Preferred substituents of the benzene ring, when $R_L$ is phenyl, include:

(i) acylamido, wherein the amide substituent is selected from $C_{1-7}$ alkyl, $C_{3-20}$ heterocyclyl, and $C_{5-20}$ aryl, more preferably $C_{1-7}$ alkyl and $C_{5-20}$ aryl, which groups are optionally further substituted. The optional substituents may be selected from any of those listed above, but those of particular interest include $C_{1-7}$ alkyl and $C_{5-20}$ aryl groups, halo, ether, thioether and sulfone groups;

(ii) ureido, where one amine substituent is preferably hydrogen, and the other is selected from $C_{1-7}$ alkyl, $C_{3-20}$ heterocyclyl, and $C_{5-20}$ aryl, more preferably $C_{1-7}$ alkyl and $C_{5-20}$ aryl, which groups are optionally further substituted. The optional substituents may be selected from any one of those listed above, but those of particular interest include $C_{1-7}$ alkyl, $C_{3-20}$ heterocyclyl and $C_{5-20}$ aryl groups, halo and ether groups;

(iii) sulfonamino, wherein the amine substituent is preferably hydrogen and the sulfone substituent is selected from $C_{1-7}$ alkyl, $C_{3-20}$ heterocyclyl, and $C_{5-20}$ aryl, more preferably $C_{1-7}$ alkyl and $C_{5-20}$ aryl, which groups are optionally further substituted. The optional substituents may be selected from any of those listed above, but those of particular interest include $C_{5-20}$ aryl groups and acylamido groups;

(iv) acyloxy, wherein the acyloxy substituent is selected from $C_{1-7}$ alkyl, $C_{3-20}$ heterocyclyl, and $C_{5-20}$ aryl, more preferably $C_{1-7}$ alkyl and $C_{5-20}$ aryl, which groups are optionally further substituted. The optional substituents may be selected from any of those listed above, but those of particular interest include $C_{1-7}$ alkyl and $C_{5-20}$ aryl groups, halo, ether, thioether, sulfone and nitro groups.

If A and B together represent a substituted fused aromatic ring, it is preferred that the substituent does not form an intra ring link with a substituent on a ring which forms part of $R_c$. Substituents in the five position are particularly preferred.

In particular, when $R_L$ is —$CH_2$-phenyl, the phenyl group is preferably substituted.

Where appropriate, the above preferences may be taken in combination with each other.

Preferred Compounds

The following compounds are preferred embodiments of the first aspect of the invention:

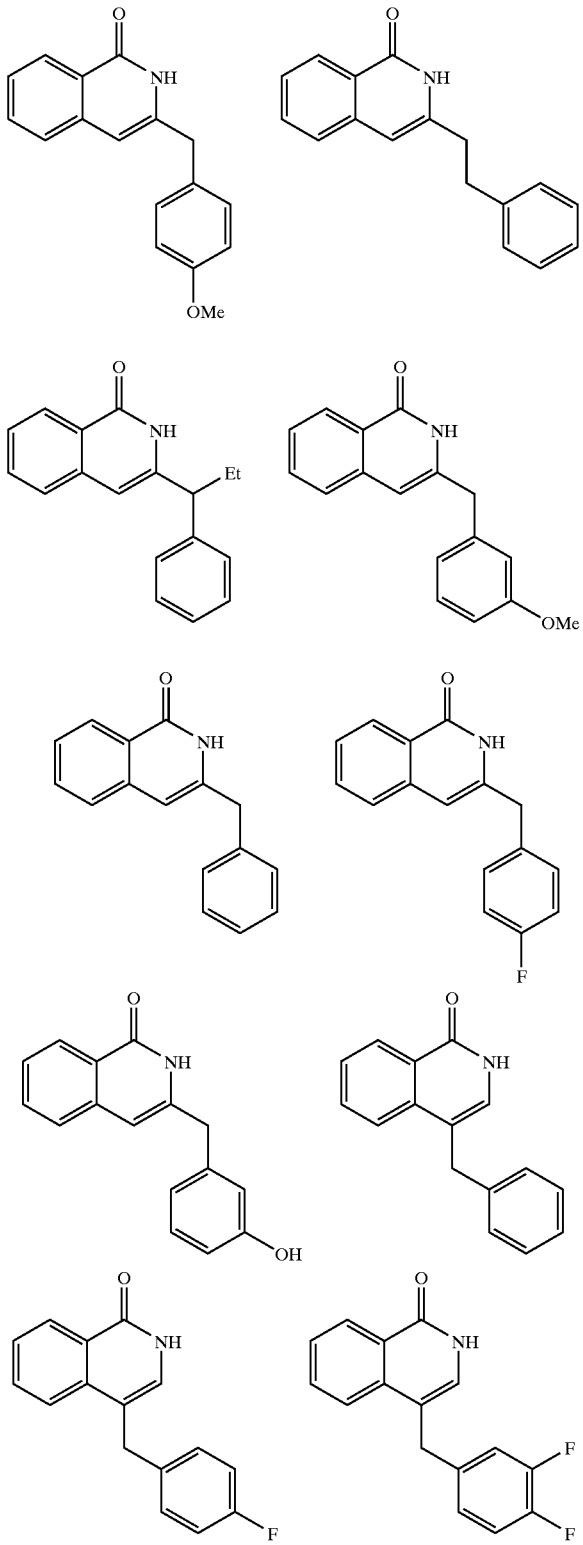

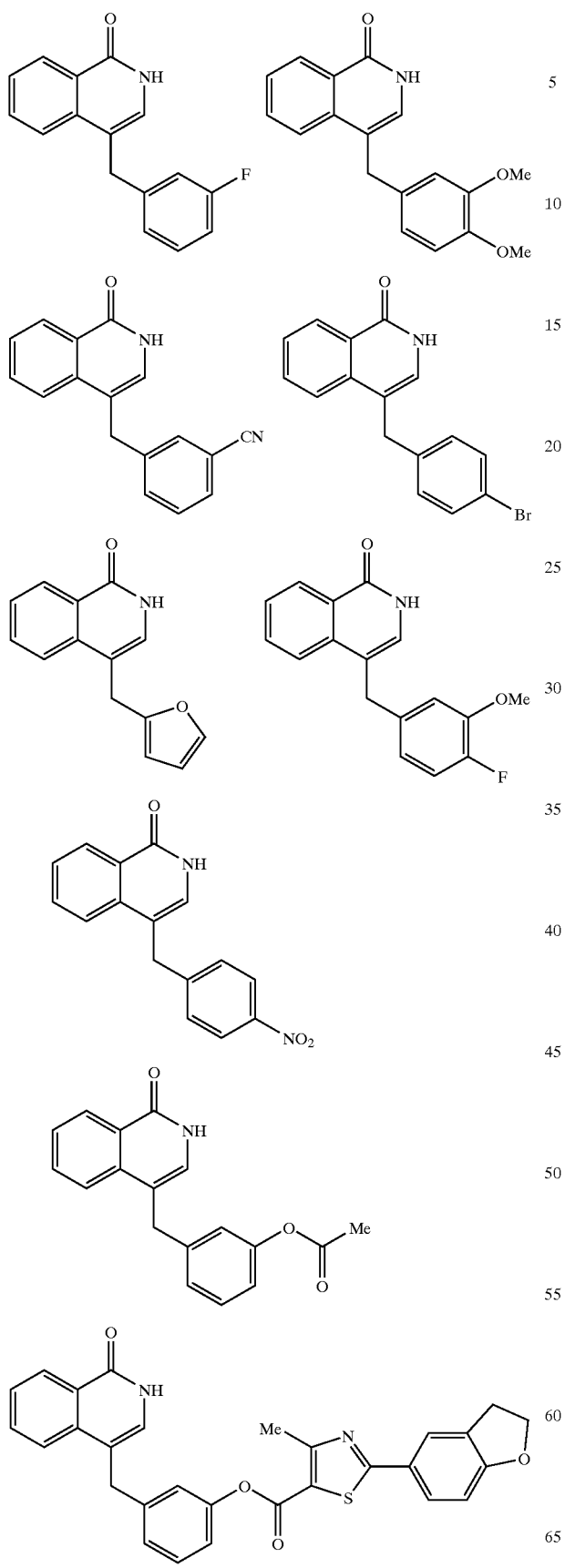
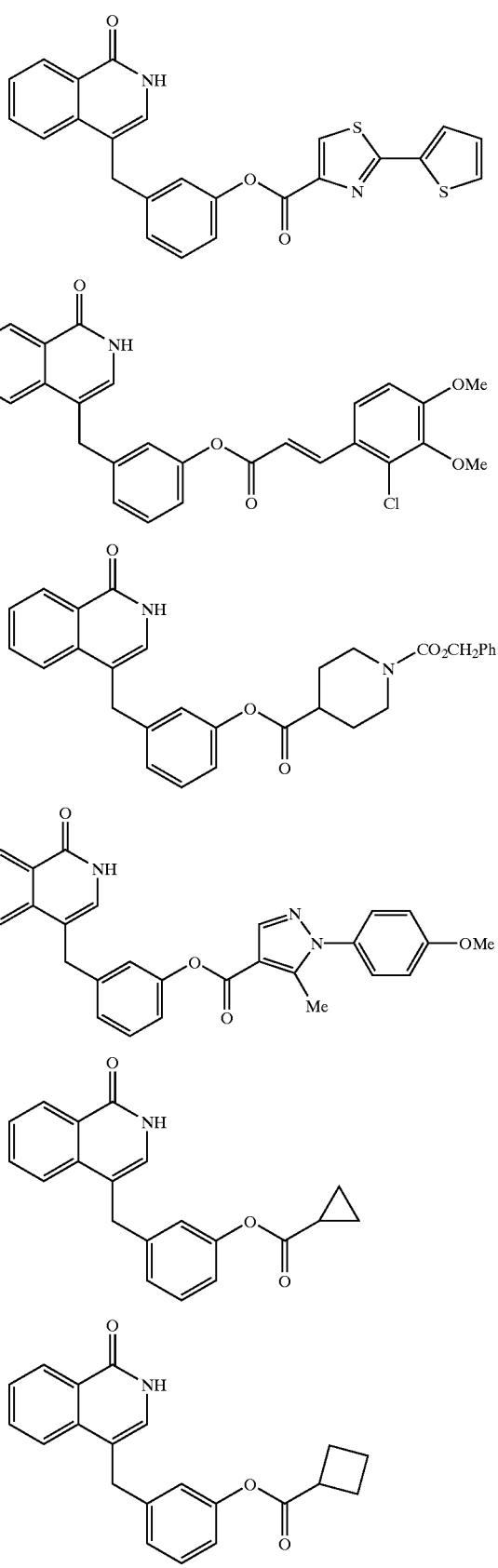

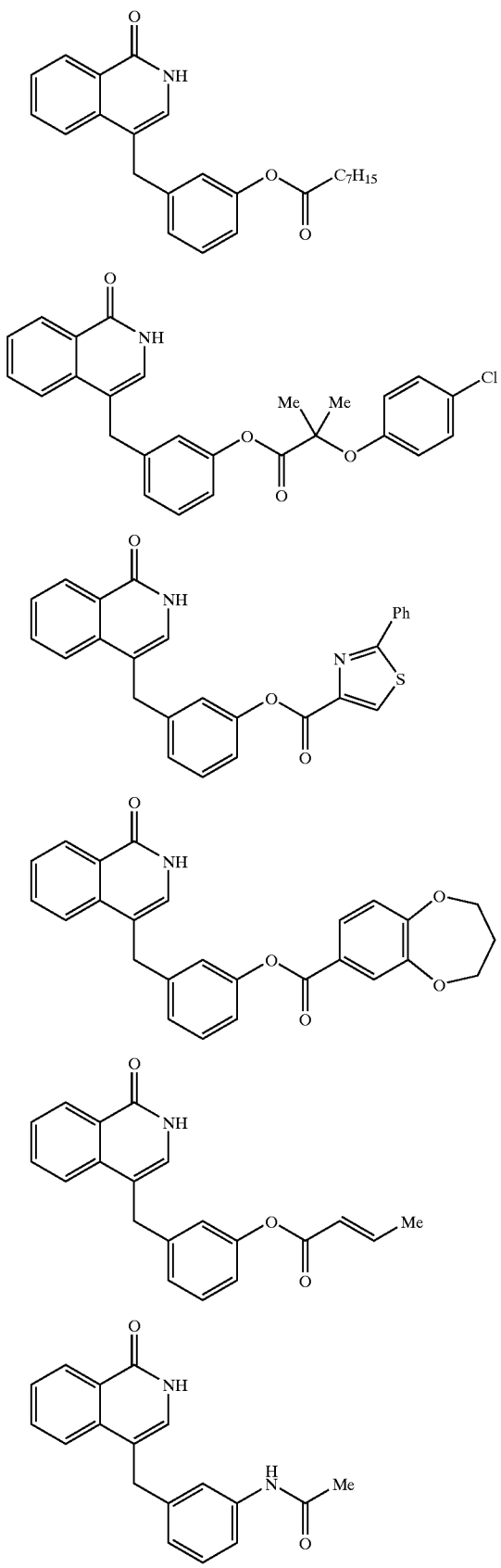
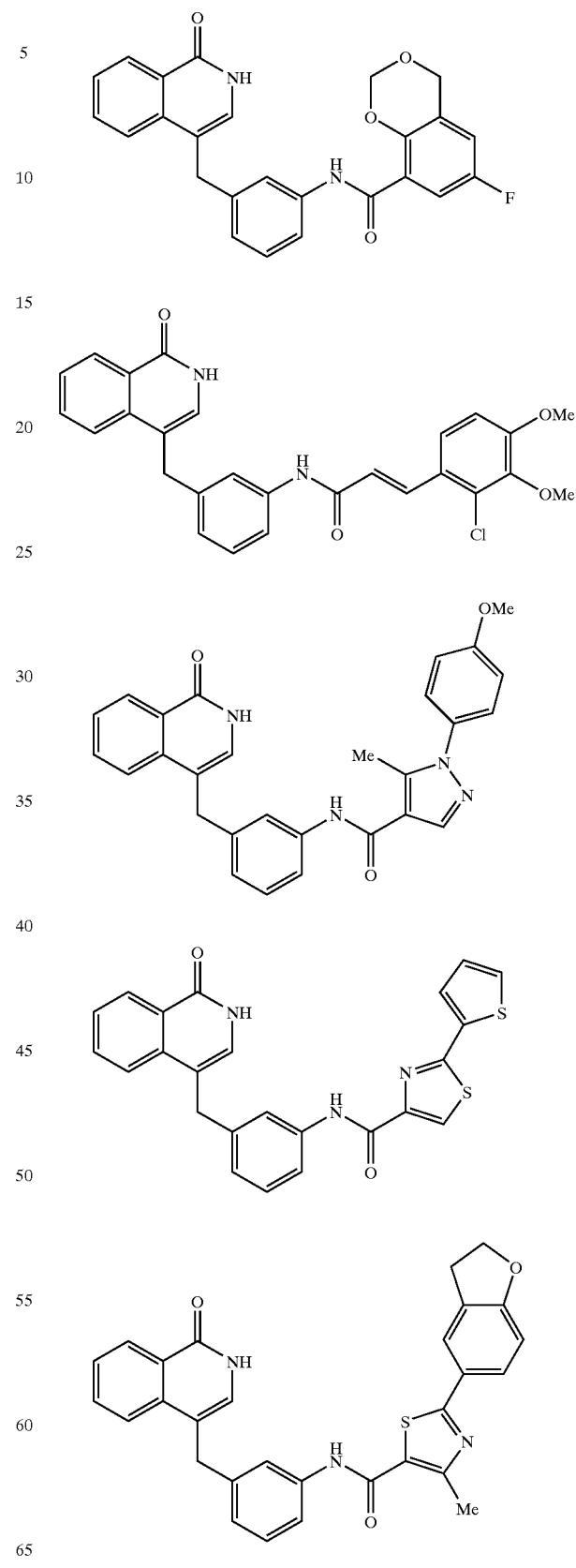

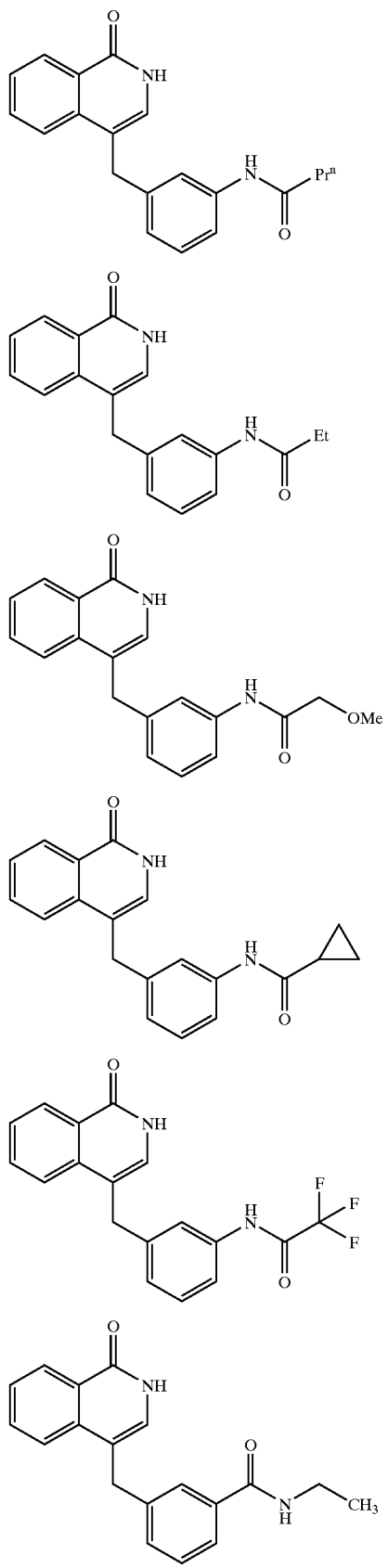
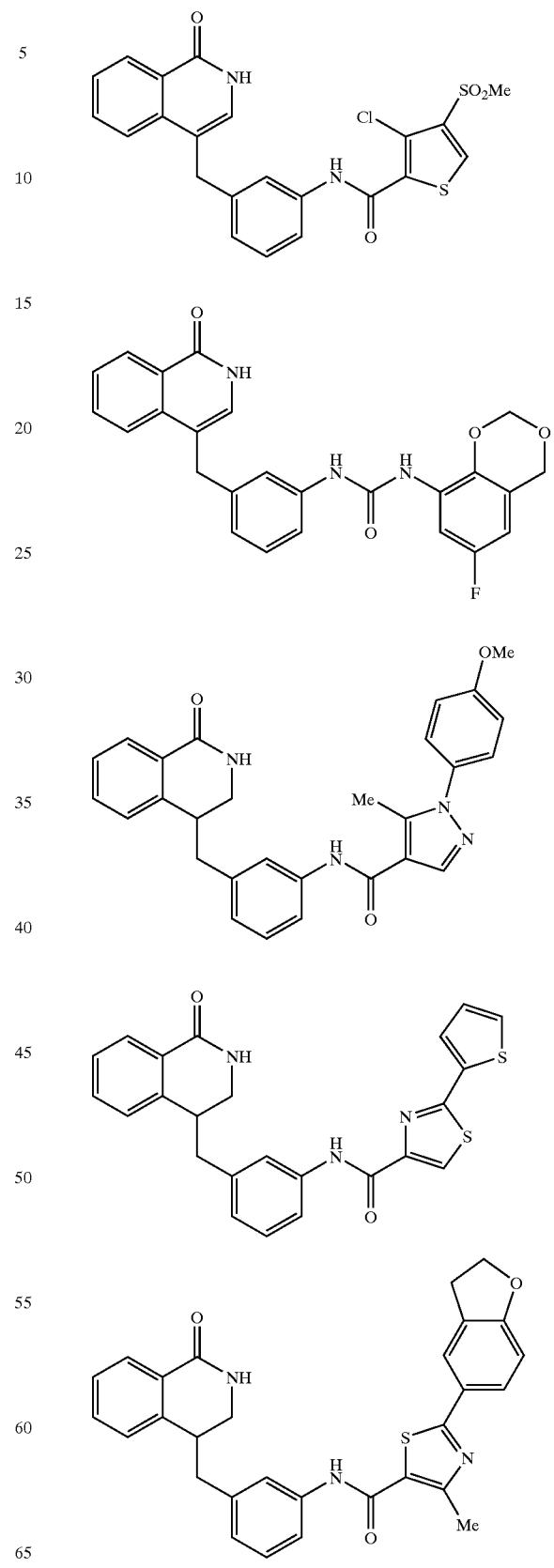

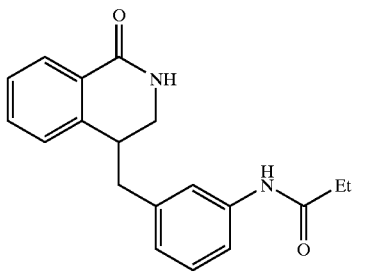
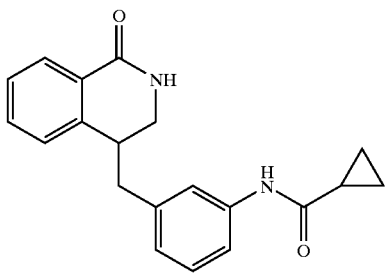
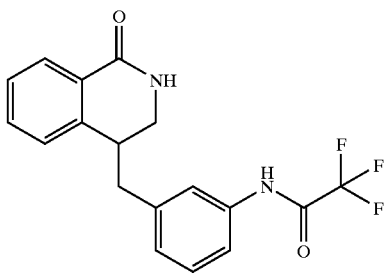
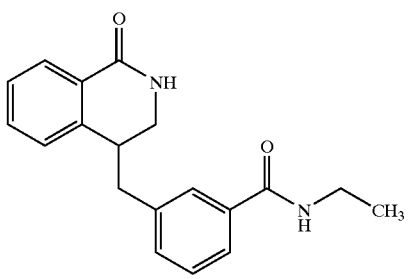
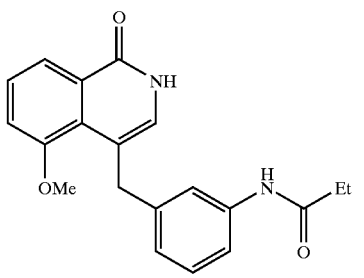
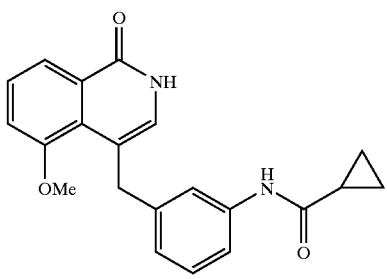
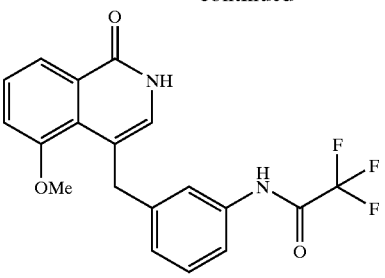
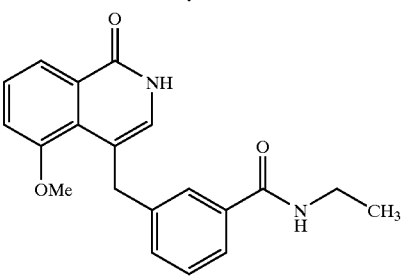

Includes Other Forms

Included in the above are the well known ionic, salt, solvate, and protected forms of these substituents. For example, a reference to carboxylic acid (—COOH) also includes the anionic (carboxylate) form (—COO⁻), a salt or solvate thereof, as well as conventional protected forms. Similarly, a reference to an amino group includes the protonated form (—N⁺HR¹R²), a salt or solvate of the amino group, for example, a hydrochloride salt, as well as conventional protected forms of an amino group. Similarly, a reference to a hydroxyl group also includes the anionic form (—O⁻), a salt or solvate thereof, as well as conventional protected forms of a hydroxyl group.

Isomers, Salts, Solvates, Protected Forms, and Prodrugs

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope- and halfchair-forms; and combinations thereof, hereinafter collectively referred to as "isomers" (or "isomeric forms").

If the compound is in crystalline form, it may exist in a number of different polymorphic forms.

Note that, except as discussed below for tautomeric forms, specifically excluded from the term "isomers," as used herein, are structural (or constitutional) isomers (i.e. isomers which differ in the connections between atoms rather than merely by the position of atoms in space). For example, a reference to a methoxy group, —OCH₃, is not to be construed as a reference to its structural isomer, a hydroxymethyl group, —CH₂OH. Similarly, a reference to ortho-chlorophenyl is not to be construed as a reference to its structural isomer, meta-chlorophenyl. However, a reference to a class of structures may well include structurally isomeric forms falling within that class (e.g. $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hyroxyazo, and nitro/aci-nitro.

Particularly relevant to the present invention is the tautomeric pair that exists when RN is H, illustrated below:

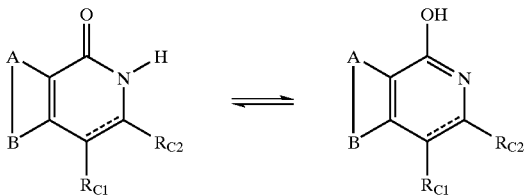

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1–19.

For example, if the compound is anionic, or has a functional group which may be anionic (e.g. —COOH may be —COO$^-$), then a salt may be formed with a suitable cation. Examples of suitable inorganic cations include, but are not limited to, alkali metal ions such as Na+ and K$^+$, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: acetic, propionic, succinic, gycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, toluenesulfonic, methanesulfonic, ethanesulfonic, ethane disulfonic, oxalic, isethionic, valeric, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form," as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts, Wiley, 1991).

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide (>NO•).

For example, a carboxylic acid group may be protected as an ester for example, as: an C$_{1-7}$ alkyl ester (e.g. a methyl ester; a t-butyl ester); a C$_{1-7}$ haloalkyl ester (e.g. a C$_{1-7}$ trihaloalkyl ester); a triC$_{1-7}$alkylsilyl-C$_{1-7}$alkyl ester; or a C$_{5-20}$ aryl-C$_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug", as used herein, pertains to a compound which, when metabolised (e.g. in vivo), yields the desired active compound. Typically, the prodrug is inactive, or less active than the active compound, but may provide advantageous handling, administration, or metabolic properties.

For example, some prodrugs are esters of the active compound (e.g. a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required. Examples of such metabolically labile esters include those wherein R is $C_{1-7}$alkyl (e.g. -Me, -Et); $C_{1-7}$ aminoalkyl (e.g. aminoethyl; 2-(N,N-diethylamino)ethyl; 2-(4-morpholino)ethyl); and acyloxy-$C_{1-7}$alkyl (e.g. acyloxymethyl; acyloxyethyl; e.g. pivaloyloxymethyl; acetoxymethyl; 1-acetoxyethyl; 1-(1-methoxy-1-methyl)ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy) carbonyloxyethyl; (4-tetrahydropyranyl)carbonyloxymethyl; and 1-(4-tetrahydropyranyl)carbonyloxyethyl). Further suitable prodrug forms include phosphonate and glycolate salts.

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Acronyms

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether ($Et_2O$), acetic acid (AcOH), dichloromethane (methylene chloride, DCM), trifluoroacetic acid (TFA), dimethylformamide (DMF), tetrahydrofuran (THF), and dimethylsulfoxide (DMSO).

Synthesis

Compounds as described in the first aspect can be synthesised by a number of methods, examples of some of which are given below.

The following papers provide routes to compounds within the general class illustrated (where Ar=$C_{5-20}$ aryl) and these papers are herein incorporated by reference.

I. W. Elliott and Y. Takekoshi, *J. Heterocyclic Chem.*, 1976, 13, 597.

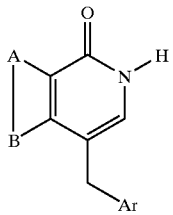

K. Masayasu, I. Waki, Y. Deguchi, K. Amemiya and T. Maeda, *Chem. Pharm. Bull.*, 1983, 31(4), 1277.

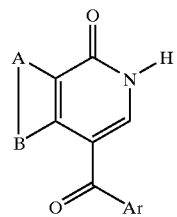

The formed aromatic ring (represented by -A-B-) is usually derivatised before the main synthesis steps, and starting materials with the desired structure and substituent pattern are either commercially available or readily synthesised.

The main synthesis steps may lead to compounds where $R_N$ is H. The possible substituents at this position can be added by the use of an appropriate electrophile with suitable reaction conditions.

Further derivatisation of the groups on $R_{C1}$ and $R^{C2}$ can be carried out using conventional methods.

Synthesis of 3-Substituted Isoquinolinones

Compounds of the present invention in which $R_{C1}$ is H and $R_{C2}$, $R_N$, A and B are as defined in the first aspect and the bond joining positions 3 and 4 is a double bond, may be synthesised by reaction of a compound of Formula 1:

Formula 1

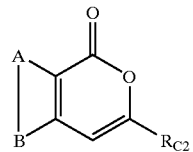

in which $R_{C2}$, A and B are as previously defined, with a compound of formula $R_N NH_2$, in which $R_N$ is as previously defined, at a temperature in the range of 100–200° C., optionally in a sealed vessel so as to generate high pressure, optionally in the presence of a solvent, for example methanol.

Compounds of Formula 1 may be synthesised by reaction of a compound of Formula 2:

Formula 2

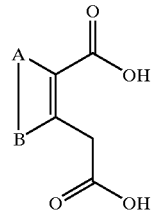

in which A and B are as defined above, with a compound of formula $R_{C2}$COX, in which $R_{C2}$ is as previously defined and X is a leaving group, for example a halogen such as chlorine, at a temperature in the range of 100–250° C., optionally in the presence of a solvent, for example xylene.

Compounds of Formula 2 are commercially available or may be readily prepared by known methods.

Synthesis of 4-Substituted Isoquinolinones

Compounds of the present invention in which $R_{C1}$ is an arylalkyl group of formula $R_L CHR_1$— in which $R_L$ and $R_1$ are as defined in the first aspect, $R_{C2}$ and $R_N$ are H and A and B are as defined in the first aspect and the bond joining positions 3 and 4 is a double bond, may be synthesised by reaction of a compound of Formula 3:

Formula 3

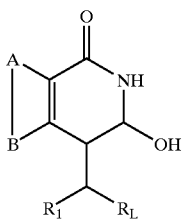

in which A, B, $R_L$ and $R_1$ are as previously defined, with a dehydrating agent, for example toluene-4-sulphonic acid, at a temperature in the range of 20–150° C., optionally in the presence of a solvent, for example toluene.

Compounds of Formula 3 may be synthesised by reaction of a compound of Formula 4:

Formula 4

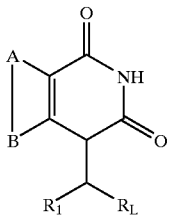

in which A, B, $R_L$ and $R_1$ are as previously defined with a reducing agent, for example a source of hydride such as sodium borohydride, in a solvent, for example methanol, at a temperature in the range of −20° C. to the boiling point of the chosen solvent.

Compounds of Formula 4 may be synthesised by reduction of a compound of Formula 5:

Formula 5

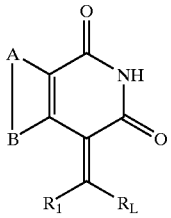

in which A, B, $R_L$ and $R_1$ are as previously defined with a reducing agent, for example hydrogen, in the presence of an appropriate catalyst, for example palladium-on-carbon, in the presence of a solvent, for example methanol, at a temperature in the range of 20° C. to the boiling point of the chosen solvent, optionally under increased pressure.

Compounds of Formula 3 may also be synthesised directly from Compounds of Formula 5 by reaction with a reducing agent, for example a source of hydride such as sodium borohydride, in a solvent, for example methanol, at a temperature in the range of −20° C. to the boiling point of the chosen solvent.

Compounds of Formula 5 may be synthesised by reaction of a compound of Formula 6:

Formula 6

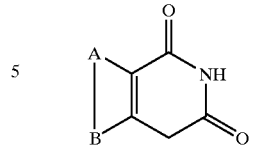

in which A and B are as previously defined, with a carbonyl compound of Formula $R_L COR_1$ in which $R_L$ and $R_1$ are as previously defined, in the presence of a base, for example piperidine, optionally in the presence of a solvent, for example acetic acid, at a temperature in the range of 20° C. to the boiling point of the chosen solvent.

Compounds of Formula 6 may be synthesised by reaction of a compound of Formula 2 with urea at a temperature in the range of 150–190° C.

Synthesis of 3- or 4-Substituted 3,4-dihydroisoquinolones

Compounds of the present invention in which the bond joining positions 3 and 4 is a single bond (i.e. Compounds of Formula 7):

Formula 7

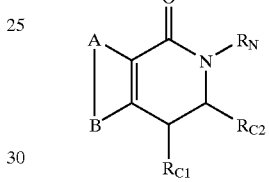

in which $R_{C1}$, $R_{C2}$, $R_N$, A and B are as defined in the first aspect may be synthesised by reduction of Compounds of the present invention in which the bond joining positions 3 and 4 is a double bond (i.e. Compounds of Formula 8):

Formula 8

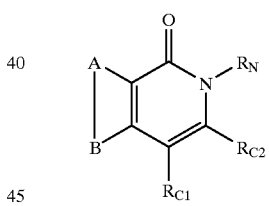

in which $R_{C1}$, $R_{C2}$, $R_N$, A and B are as defined in the first aspect with a reducing agent, for example hydrogen or ammonium formate, in the presence of an appropriate catalyst, for example palladium-on-carbon or Raney Nickel, in the presence of a solvent, for example ethanol or acetic acid, at a temperature in the range of 20° C. to the boiling point of the chosen solvent, optionally under increased pressure.

Use

The present invention provides active compounds, specifically, active in inhibiting the activity of PARP.

The term 'active', as used herein, pertains to compounds which are capable of inhibiting PARP activity, and specifically includes both compounds with intrinsic activity (drugs) as well as prodrugs of such compounds, which prodrugs may themselves exhibit little or no intrinsic activity.

One assay which may conveniently be used in order to assess the PARP inhibition offered by a particular compound is described in the examples below.

The present invention further provides a method of inhibiting the activity of PARP in a cell, comprising contacting said cell with an effective amount of an active compound, preferably in the form of a pharmaceutically acceptable composition. Such a method may be practised in vitro or in vivo.

For example, a sample of cells may be grown in vitro and an active compound brought into contact with said cells, and the effect of the compound on those cells observed. As examples of "effect" the amount of DNA repair effected in a certain time may be determined. Where the active compound is found to exert an influence on the cells, this may be used as a prognostic or diagnostic marker of the efficacy of the compound in methods of treating a patient carrying cells of the same cellular type.

The term "treatment" as used herein in the context of treating a condition pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "adjunct" as used herein relates to the use of active compounds in conjunction with known therapeutic means. Such means include cytotoxic regimes of drugs and/or ionising radiation as used in the treatment of different cancer types.

The term "therapeutically-effective amount", as used herein, pertains to that amount of an active compound, or a material, composition or dosage from comprising an active compound, which is effective for producing some desired therapeutic effect, commensurate with a reasonable benefit/risk ratio.

Active compounds may also be used as cell culture additives to inhibit PARP, for example, in order to radiosensitize cells to known chemo or ionising radiation treatments in vitro.

Active compounds may also be used as part of an in vitro assay, for example, in order to determine whether a candidate host is likely to benefit from treatment with the compound in question.

Administration

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutang, gibbon), or a human.

Formulations

While it is possible for the active compound to be administered alone, it is preferable to present it as a pharmaceutical composition (e.g. formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, *Remington's Pharmaceutical Sciences*, 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g. compression or molding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavored basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichorotetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e. an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 µg/ml, for example from about 10 ng/ml to about 1 µg/ml. The formulations may be presented in unit-dose or multidose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 µg to about 250 mg per kilogram body weight of the subject per day. Where the active compound is a salt, an ester, prodrug, or the like, the amount administered is calculated on the basis of the parent compound and so the actual weight to be used is increased proportionately.

EXAMPLES

The following are examples are provided solely to illustrate the present invention and are not intended to limit the scope of the invention, as described herein.

Synthesis Data

The following compounds were synthesised using the routes set out above:

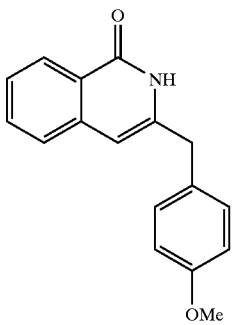

1

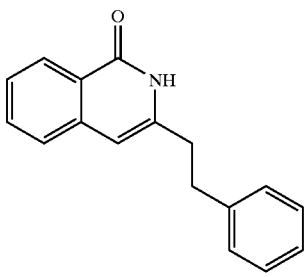

2

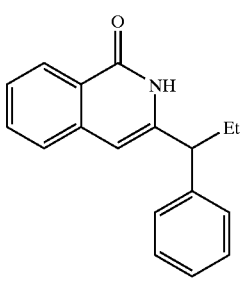

3

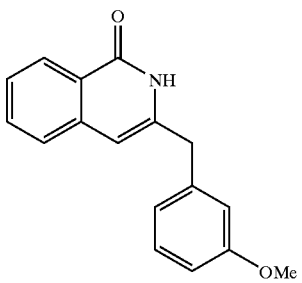

4

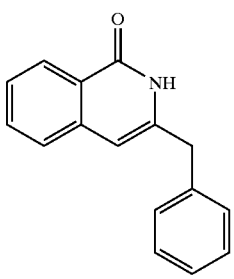

5

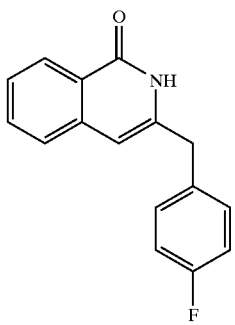
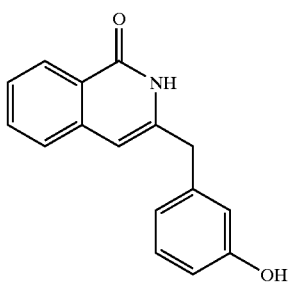
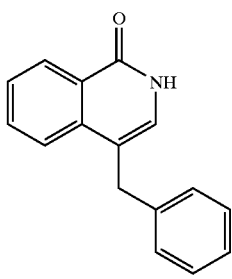
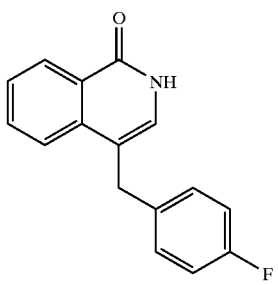
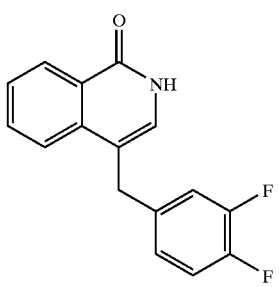
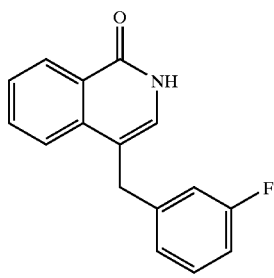
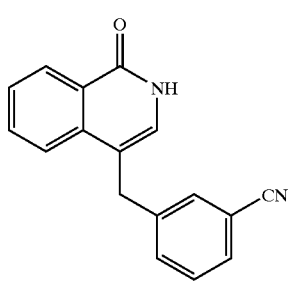
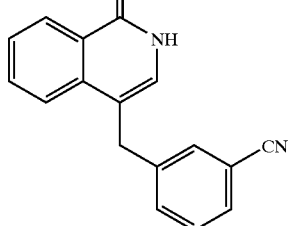
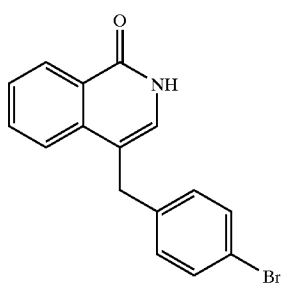
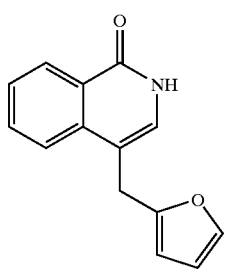
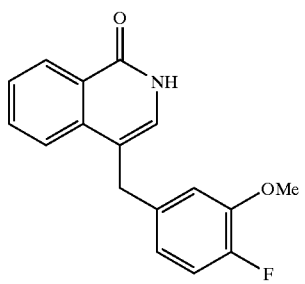

-continued

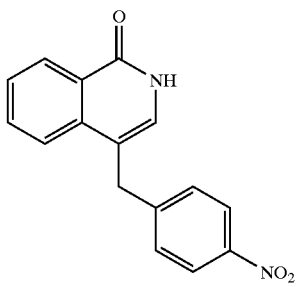

Synthesis of 3-Substituted Isoquinolinones
Compound 1 ($R_{C2}$=4-methoxybenzyl, $R_{C1}$ and $R_{N}$=H)
Step 1

A well-stirred mixture of homophthalic acid (10 g; 56 mmol) and 2-(4-methoxyphenyl)acetyl chloride (10 g, 230 mmol) was heated at 200° C. for 3 hours under nitrogen then cooled to 50° C. and dissolved in toluene (100 ml), The solvent was removed in vacuo and the residue was dissolved in methanol (100 ml). Silica (30 g) was added and the solvent was removed in vacuo. The crude product, thereby adsorbed onto silica, was applied to the top of a column of silica and purified by chromatography using 10–50% mixtures of ethyl acetate and hexane as eluant. Appropriate fractions were combined and the solvents removed in vacuo to give 3-(4-methoxybenzyl)isocoumarin (0.9 g, 26%) as an oil; $δ_H$ 3.75 (3H, s), 3.80 (2H, s), 6.50 (1H, s), 6.95 (2H, d, J=8.9 Hz), 7.30 (2H, d, J=8.9 Hz), 7.40–7.90 (3H, m), 8.10 (1H, d); m/z (M+H)$^{+\cdot}$ 267.
Step 2

A stirred suspension of 3-(4-methoxybenzyl)isocoumarin (0.35 g, 1.3 mmol) in 15% methanolic ammonia solution (100 ml) was heated at 150° C. in a 300 ml autoclave for 5 hours then cooled to ambient temperature. The resulting solid was collected by filtration, washed with a little cold methanol and dried in vacuo to give 3-(4-methoxybenzyl)-1-isoquinolinone (0.04 g, 12%) as a solid; m.pt. 216–218° C.; $δ_H$ 3.80 (3H, s), 3.85 (2H, s), 6.25 (1H, s), 6.90 (2H, d, J=8.2 Hz), 7.30 (2H, d), 7.30–7.60 (3H, m), 8.20 (1H, d), 11.20 (1H, br s); m/z (M+H)$^{+\cdot}$ 266 (100% purity).

Compounds 2–6 were prepared in a manner similar to that described above for Compound 1:
Compound 2 ($R_{C2}$=2-phenylethyl, $R_{C1}$ and $R_{N}$=H)
Step 1

3-(2-Phenylethyl)isocoumarin. Yield, 16%; oil; $δ_H$ 2.60–3.20 (4H, m), 6.20 (1H, s), 7.05–7.75 (8H, m), 8.25 (1H, d); m/z (M+H)$^{+\cdot}$ 251.
Step 2

3-(2-Phenylethyl)-1-isoquinolinone. Yield, 35%; m.pt. 198–200° C.; $δ_H$ 2.70–3.10 (4H, m), 6.40 (1H, s), 7.20–7.70 (8H, m), 8.20 (1H, d), 11.20 (1H, br s); m/z (M+H)$^{+\cdot}$ 250 (100% purity).
Compound 3 ($R_{C2}$=1-phenylpropyl, $R_{C1}$ and $R_{N}$=H)
Step 1

3-(1-Phenylpropyl)isocoumarin. Yield, 14%; oil; $δ_H$ 0.95 (3H, t), 2.10 (2H, q), 3.60 (1H, t), 6.30 (1H, s), 7.20–7.80 (8H, m), 8.20 (1H, d).
Step 2

3-(1-Phenylpropyl)-1-isoquinolinone. Yield, 43%; m.pt. 179–180° C.; $δ_H$ 0.95 (3H, t), 2.10 (2H, m), 3.60 (1H, t), 6.30 (1H, s), 7.20–7.80 (8H, m), 8.20 (1H, d), 11.10 (1H, br s); m/z (M+H)$^{+\cdot}$ 264 (97% purity).
Compound 4 ($R_{C2}$=3-methoxybenzyl, $R_{C1}$ and $R_{N}$=H)
Step 1

3-(3-Methoxybenzyl)isocoumarin. Yield, 33%; oil; $δ_H$ 3.75 (3H, s), 3.80 (2H, s), 6.20 (1H, s), 6.60–6.95 (2H, m), 7.10–7.65 (5H, m), 8.20 (1H, d).

Step 2

3-(3-Methoxybenzyl)-1-isoquinolinone. Yield, 45%; m.pt. 208–210° C.; $δ_H$ 3.70 (3H, s), 3.75 (2H, s), 6.35 (1H, s), 6.80–7.60 (6H, m), 8.15 (1H, d), 10.90 (1H, br s); m/z (M+H)$^{+\cdot}$ 266 (100% purity).
Compound 5 ($R_{C2}$=benzyl, $R_{C1}$ and $R_{N}$=H)
Step 1

3-Benzylisocoumarin. Yield, 60%; oil; $δ_H$ 3.80 (2H, s), 6.15 (1H, s), 7.05–7.60 (8H, m), 8.20 (1H, d)
Step 2

3-Benzyl-1-isoquinolinone. Yield, 31%; m.pt. 193–195° C.; $δ_H$ 3.75 (2H, s), 6.35 (1H, s), 7.15–7.60 (8H, m), 8.15 (1H, d), 11.30 (1H, br s); m/z (M+H)+236 (100% purity).
Compound 6 ($R_{C2}$=4-fluorobenzyl, $R^{C1}$ and $R_{N}$=H)
Step 1

3-(4-Fluorobenzyl)isocoumarin. Yield, 29%; oil; $δ_H$ 3.80 (2H, s), 6.30 (1H, s), 7.00–7.70 (7H, m), 8.25 (1H, d).
Step 2

3-(4-Fluorobenzyl)-1-isoquinolinone. Yield, 79%; m.pt. 238–240° C.; $δ_H$ 3.80 (2H, s), 6.40 (1H, s), 7.00–7.60 (7H, m), 8.15 (1H, d), 11.30 (1H, br s); m/z (M+H)$^{+\cdot}$ 254.
Compound 7 ($R_{C2}$=3-hydroxybenzyl, $R_{C1}$ and $R_{N}$=H)

A solution of boron tribromide in dichloromethane (1M; 8.5 ml, 8.5 mmol) was added dropwise under nitrogen to an ice-cooled, stirred suspension of 3-(3-methoxybenzyl) isoquinolinone (1 g, 3.8 mmol) in dichloromethane (5 ml), the stirred mixture was heated under reflux for 6 hours, then it was cooled to ambient temperature and poured onto 10% aqueous sodium hydroxide solution (30 ml). The basic solution was washed with dichloromethane (3×50 ml), then it was acidified by the addition of concentrated hydrochloric acid. The product was extracted into ethyl acetate (3×50 ml), the combined extracts were dried (MgSO$_4$) and the solvent was removed in vacuo to leave 3-(3-hydroxybenzyl) isoquinolinone (0.4 g, 42%) as a white solid; m.pt. 225–227° C.; $δ_H$ 3.80 (2H, s), 6.35 (1H, s), 6.60–7.70 (7H, m), 8.10 (1H, d), 9.30 (1H, s), 11.20 (1H, br s); m/z (M+H)$^{+\cdot}$ 252 (100% purity).
Synthesis of 4-Substituted Isoquinolinones
Compound 8 ($R_{C1}$=benzyl, $R_{C2}$ and $R_{N}$=H)
Step 1

A mixture of homophthalic acid (200 g, 1.09 mol) and urea (80 g, 1.31 mol) was ground to a fine powder then heated at 175–185° C. until it had melted then resolidified. The mixture was cooled to ambient temperature, methanol (500 ml) was added, then the mixture was heated under reflux for 20 minutes, filtered, and allowed to cool to ambient temperature. The resulting solid was collected by filtration, washed with methanol and dried in vacuo to give homophthalimide (60 g, 34%) as a solid; m.pt. 235–240° C.; $δ_H$ 4.0 (2H, s), 7.3–7.75 (3H, m), 8.10 (1H, d), 11.20 (1H, br s).
Step 2

A stirred mixture of homophthalimide (15 g, 93 mmol), benzaldehyde (9.9 g, 93 mmol), piperidine (9 ml) and acetic acid (465 ml) was heated under reflux for 1 hour, cooled to ambient temperature and diluted with water (500 ml). The resulting solid was collected by filtration, washed with water and dried in vacuo to give 4-benzylidenehomophthalimide (18.5 g, 82%) as a solid; m.pt. 173–177° C. Used crude for the next step.
Step 3

Sodium borohydride (1.2 g, 32 mmol) was added in portions to a stirred suspension of 4-benzylidenehomophthalimide (2 g, 8 mmol) in methanol (50 ml), then the stirred mixture was heated under reflux for 4 hours, cooled to ambient temperature and added to water (200 ml). The product was extracted into ethyl acetate (3×50 ml), the combined extracts were washed with water (2×30 ml), dried (MgSO$_4$) and the solvent was removed in vacuo. The residue was dissolved in the minimum volume of ether and sufficient hexane was added to precipitate the product. The resulting solid was collected by filtration, washed with hexane (20 ml) and dried in vacuo to give the 4-benzyl-3-hydroxy-3,4-dihydro-1-isoquinolinone intermediate which was used without purification.

A stirred mixture of the above intermediate (0.1 g, 0.4 mmol), toluene-4-sulphonic acid (10 mg) and toluene (50 ml) was heated under reflux for 4 hours while water was removed from the reaction by azeotropic distillation. The mixture was allowed to cool to ambient temperature, then it was washed with saturated aqueous sodium hydrogencarbonate solution (2×30 ml) and water (2×30 ml), dried (MgSO$_4$), and the solvent was removed in vacuo to give 4-benzyl-1-isoquinolinone (0.02 g, 3% over two stages) as a solid; m.pt. 217–220° C.; $\delta^H$ 4.0 (2H, s), 7.0 (1H, s), 7.15–7.3 (5H, m), 7.45 (1H, m), 7.65 (2H, m), 8.25 (1H, d), 11.20 (1H, br s).

Compounds 9–16 were prepared in a manner similar to that described above for Compound 8 except that for Compounds 10–17, purification via preparative-scale high performance liquid chromatography was required for the isolation of pure material.

Compound 9 ($R_{C1}$=4-fluorobenzyl, $R_{C2}$ and $R_N$=H)
Step 1
As for Compound 8
Step 2
4-(4-Fluorobenzylidene)homophthalimide. Yield, 100%; m.pt. 187–191° C.; $\delta_H$ 7.1–8.2 (9H, m), 11.3–11.7 (1H, br d).
Step 3
4-(4-Fluorobenzyl)-1-isoquinolinone. Yield, 8% over two stages; m.pt. 185–188° C.; $\delta_H$ 4.0 (2H, s), 6.9–7.7 (8H, m), 8.25 (1H, d), 11.20 (1H, br s); m/z (M+H)$^{+\cdot}$ 254.

Compound 10 ($R_{C1}$=3,4-difluorobenzyl, $R_{C2}$ and $R_N$=H)
Step 1
As for Compound 8
Step 2
4-(3,4-Difluorobenzylidene)homophthalimide. Yield, 76%; m.pt. 199–205° C.; $\delta_H$ 7.1–8.2 (8H, m), 11.3–11.7 (1H, br d).
Step 3
4-(3,4-Difluorobenzyl)-1-isoquinolinone. Crude yield, 16% over two stages; m.pt. 148–150° C.; m/z (M+H)$^{+\cdot}$ 272 (31% purity). Purified by preparative scale high performance liquid chromatography on a Gilson LC unit under the following conditions: Column—Jones Chromatography Genesis 4$\mu$ C18 column, 10 mm×250 mm; Mobile phase A—0.1% aqueous TFA; Mobile phase B—acetonitrile; Flow rate 6 ml/min; Gradient—starting at 90% A/10% B for one minute, rising to 97% B after 15 minutes, holding there for 2 minutes, then back to the starting conditions. Peak acquisition was based on UV detection at 254 nm and compound identification was by mass spectroscopy on a Finnegan LCQ in positive ion mode. Retention time—4.04 minutes; m/z (M+H)$^{+\cdot}$ 272.

Compound 11 ($R_{C1}$=3-fluorobenzyl, $R_{C2}$ and $R_N$=H)
Step 1
As for Compound 8
Step 2
4-(3-Fluorobenzylidene)homophthalimide. Yield, 79%; m.pt. 174–176° C.; $\delta_H$ 7.1–7.6 (7H, m), 7.95–8.2 (2H, m), 11.3–11.7 (1H, br d).
Step 3
4-(3-Fluorobenzyl)-1-isoquinolinone. Crude yield, 14% over two stages; m.pt. 132–134° C.; m/z (M+H)$^{+\cdot}$ 254 (37% purity) Purified by preparative scale high performance liquid chromatography on a Gilson LC unit under the following conditions: Column—Jones Chromatography Genesis 4$\mu$ C18 column, 1 mm×250 mm; Mobile phase A—0.1% aqueous TFA; Mobile phase B—acetonitrile; Flow rate 6 ml/min; Gradient—starting at 90% A/10% B for one minute, rising to 97% B after 15 minutes, holding there for 2 minutes, then back to the starting conditions. Peak acquisition was based on UV detection at 254 nm and compound identification was by mass spectroscopy on a Finnegan LCQ in positive ion mode. Retention time—3.91 minutes; m/z (M+H)$^{+\cdot}$ 254.

Compound 12 ($R_{C1}$=3-cyanobenzyl, $R_{C2}$ and $R_N$=H)
Step 1
As for Compound 8
Step 2
4-(3-Cyanobenzylidene)homophthalimide. Yield, 90%; m.pt. 272–275° C.; $\delta_H$ 7.3–8.2 (9H, m), 11.3–11.7 (1H, br d).
Step 3
4-(3-Cyanobenzyl)-1-isoquinolinone. Crude yield, 13% over two stages; m.pt. 85–88° C.; m/z (M+H)$^{+\cdot}$ 261 (31% purity). Purified by preparative scale high performance liquid chromatography on a Gilson LC unit under the following conditions: Column—Jones Chromatography Genesis 4$\mu$ C18 column, 10 mm×250 mm; Mobile phase A—0.1% aqueous TFA; Mobile phase B—acetonitrile; Flow rate 6 ml/min; Gradient—starting at 90% A/10% B for one minute, rising to 97% B after 15 minutes, holding there for 2 minutes, then back to the starting conditions. Peak acquisition was based on UV detection at 254 nm and compound identification was by mass spectroscopy on a Finnegan LCQ in positive ion mode. Retention time—3.55 minutes; m/z (M+H)+-261.

Compound 13 ($R_{C1}$ 4-bromobenzyl, $R_{C2}$ and $R_N$=H)
Step 1
As for Compound 8
Step 2
4-(4-Bromobenzylidene)homophthalimide. Yield, 86%; m.pt. 211–214° C.; $\delta_H$ 7.2–8.2 (9H, m), 11.3–11.7 (1H, br d).
Step 3
4-(4-Bromobenzyl)-1-isoquinolinone. Crude yield, 30% over two stages; m.pt. 180–182° C.; m/z (M+H)$^{+\cdot}$ 314/316 (18% purity). Purified by preparative scale high performance liquid chromatography on a Gilson LC unit under the following conditions: Column—Jones Chromatography Genesis 4$\mu$ C18 column, 10 mm×250 mm; Mobile phase A—0.1% aqueous TFA; Mobile phase B—acetonitrile; Flow rate 6 ml/min; Gradient—starting at 90% A/10% B for one minute, rising to 97% B after 15 minutes, holding there for 2 minutes, then back to the starting conditions. Peak acquisition was based on UV detection at 254 nm and compound identification was by mass spectroscopy on a Finnegan LCQ in positive ion mode. Retention time—4.22 minutes; m/z (M+H)$^{+\cdot}$ 314/316.

Compound 14 ($R_{C1}$=furfuryl, $R_{C2}$ and $R_N$=H)
Step 1
As for Compound 8
Step 2
4-Furfurylidenehomophthalimide. Yield, 92%; m.pt. 200–202° C.; $\delta_H$ 6.7 (1H, m), 7.2–8.2 (7H, m), 11.5 (1H, br s).
Step 3
4-Furfuryl-1-isoquinolinone. Crude yield, 13% over two stages; oil; m/z (M+H)$^{+\cdot}$ 226 (48% purity). Purified by preparative scale high performance liquid chromatography on a Gilson LC unit under the following conditions: Column—Jones Chromatography Genesis 4µ C18 column, 10 mm×250 mm; Mobile phase A—0.1% aqueous TFA; Mobile phase B—acetonitrile; Flow rate 6 ml/min; Gradient—starting at 90% A/10% B for one minute, rising to 97% B after 15 minutes, holding there for 2 minutes, then back to the starting conditions. Peak acquisition was based on UV detection at 254 nm and compound identification was by mass spectroscopy on a Finnegan LCQ in positive ion mode. Retention time—3.63 minutes; m/z $(M+H)^{+\cdot}$ 226.

Compound 15 ($R_{C1}$=4-fluoro-3-methoxybenzyl, $R_{C2}$ and $R_N$=H)

Step 1

As for Compound 8

Step 2

4-(4-Fluoro-3-methoxybenzylidene)homophthalimide. Yield, 80%; $\delta_H$ 3.7 (3H, s), 7.0–8.1 (8H, m), 11.4–11.7 (1H, br d).

Step 3

4-(4-Fluoro-3-methoxybenzyl)-1-isoquinolinone. Crude yield, 18% over two stages; sticky solid; m/z $(M+H)^{+\cdot}$ 284 (22% purity). Purified by preparative scale high performance liquid chromatography on a Gilson LC unit under the following conditions: Column—Jones Chromatography Genesis 4µ C18 column, 10 mm×250 mm; Mobile phase A—0.1% aqueous TFA; Mobile phase B—acetonitrile; Flow rate 6 ml/min; Gradient—starting at 90% A/10% B for one minute, rising to 97% B after 15 minutes, holding there for 2 minutes, then back to the starting conditions. Peak acquisition was based on UV detection at 254 nm and compound identification was by mass spectroscopy on a Finnegan LCQ in positive ion mode. Retention time—3.84 minutes; m/z $(M+H)^{+\cdot}$ 284.

Compound 16 ($R_{C1}$=4-nitrobenzyl, $R_{C2}$ and $R_N$=H)

Step 1

As for Compound 8

Step 2

4-(4-Nitrobenzylidene)homophthalimide. Yield, 94%; $\delta_H$ 7.1–8.3 (9H, m), 11.7 (1H, br s).

Step 3

4-(4-Nitrobenzyl)-1-isoquinolinone. Crude yield, 11% over two stages; sticky oil; m/z $(M+H)^{+\cdot}$ 281 (40% purity). Purified by preparative scale high performance liquid chromatography on a Gilson LC unit under the following conditions: Column—Jones Chromatography Genesis 4µ C18 column, 10 mm×250 mm; Mobile phase A—0.1% aqueous TFA; Mobile phase B—acetonitrile; Flow rate 6 ml/min; Gradient—starting at 90% A/10% B for one minute, rising to 97% B after 15 minutes, holding there for 2 minutes, then back to the starting conditions. Peak acquisition was based on UV detection at 254 nm and compound identification was by mass spectroscopy on a Finnegan LCQ in positive ion mode. Retention time—3.85 minutes; m/z $(M+H)^{+\cdot}$ 281.

Biological Testing

In order to assess the inhibitory action of the compounds, the following assay was used to determine $IC_{50}$ values.

Mammalian PARP, isolated from Hela cell nuclear extract, was incubated with Z-buffer (25 mM Hepes (Sigma); 12.5 mM $MgCl_2$ (Sigma); 50 mM KCl (Sigma); 1 mM DTT (Sigma); 10% Glycerol (Sigma) 0.001% NP-40 (Sigma); pH 7.4) in 96 well FlashPlates (TRADE MARK) (NEN, UK) and varying concentrations of said inhibitors added. All compounds were diluted in DMSO and gave final assay concentrations of between 10 and 0.01 µM, with the DMSO being at a final concentration of 1% per well. The total assay volume per well was 40 µl.

After 10 minutes incubation at 30° C. the reactions were initiated by the addition of a 10 µl reaction mixture, containing NAD (5 µM), $^3$H-NAD and 30mer double stranded DNA-oligos. Designated positive and negative reaction wells were done in combination with compound wells (unknowns) in order to calculate % enzyme activities. The plates were then shaken for 2 minutes and incubated at 30° C. for 45 minutes.

Following the incubation, the reactions were quenched by the addition of 50 µl 30% acetic acid to each well. The plates were then shaken for 1 hour at room temperature.

The plates were transferred to a TopCount NXT (TRADE MARK) (Packard, UK) for scintillation counting. Values recorded are counts per minute (cpm) following a 30 second counting of each well.

The % enzyme activity for each compound is then calculated using the following equation:

$$\% \text{ Inhibition} = 100 - \left(100 \times \frac{(\text{cpm of unknowns} - \text{mean negative cpm})}{(\text{mean positive cpm} - \text{mean neagative cpm})}\right)$$

The results are detailed below as $IC_{50}$ values (the concentration at which 50% of the enzyme activity is inhibited), which are determined over a range of different concentrations, normally from 10 µM down to 0.01 µM. Such $IC_{50}$ values are used as comparative values to identify increased compound potencies.

The Dose Enhancing Factor (DEF) is a ratio of the enhancement of cell growth inhibition elicited by the test compound in the presence of bleomycin compared to bleomycin alone. The test compounds were used at a fixed concentration of 25 µM. Bleomycin was used at a concentration of 0.5 µg/ml. The DEF was calculated from the formula:

$$\frac{Growth_{TC}}{Growth_{Control}} \times \frac{Growth_{bleo}}{Growth_{(bleo+TC)}}$$

where $Growth_{TC}$ is cell growth in presence of the test compound;

$Growth_{Control}$ is cell growth of control cells;

$Growth_{bleo}$ is cell growth in presence of bleomycin; and $Growth_{(bleo+TC)}$ is cell growth in presence of bleomycin and the test compound.

Cell growth was assessed using the sulforhodamine B (SRB) assay (Skehan, P., et al., 1990, *J. Natl. Cancer Inst.*, 82, 1107–1112). 2,000 HeLa cells were seeded into each well of a flat-bottomed 96-well microtiter plate in a volume of 100 µl and incubated for 6 hours at 37° C. Cells were either replaced with media alone or with media containing the test compound at a final concentration of 25 µM. Cells were allowed to grow for a further 1 hour before the addition of bleomycin to either untreated cells or test compound treated cells. Cells untreated with either bleomycin or test compound were used as a control. Cells treated with test compound alone were used to assess the growth inhibition by the test compound.

Cells were left for a further 16 hours before replacing the media and allowing the cells to grow for a further 72 hours at 37° C. The media was then removed and the cells fixed with 100 µl of ice cold 10% (w/v) trichloroacetic acid. The plates were incubated at 4° C. for 20 minutes and then washed four times with water. Each well of cells was then stained with 100 µl of 0.4% (w/v) SRB in 1% acetic acid for 20 minutes before washing four times with 1% acetic acid. Plates were then dried for 2 hours at room temperature. The dye from the stained cells was solubilized by the addition of 100 μl of 10 mM Tris Base into each well. Plates were gently shaken and left at room temperature for 30 minutes before measuring the optical density at 564 nM on a Microquant microtiter plate reader.

Results $IC_{50}$ (μM): Compound 2-0.58; Compound 4-8.5; Compound 7-1.8; Compounds 9-16≦2

DEF: Compound 1-1.15; Compound 2-1.4; Compound 4-1.2; Compound 5-1.1; Compound 7-1.2

We claim:

1. A method of treatment of a disease of the human or animal body mediated by PARP comprising administering to a subject in need thereof a therapeutically effective amount of a compound of formula:

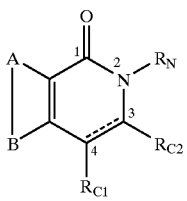

or an isomer, salt, solvate, chemically protected form, or prodrug thereof, wherein:

A and B together represent a fused benzene ring which is optionally substituted with one or more substituents selected from the group consisting of halo, nitro, hydroxy, ether, thiol, thioether, amino, $C_{1-7}$ alkyl, $C_{3-20}$ heterocyclyl, and $C_{5-20}$ aryl; wherein one or more of the substituents may together form a ring;

the dotted line between the 3 and 4 positions indicates the optional presence of a double bond;

one of $R_{C1}$ and $R_{C2}$ is represented by -L-$R_L$, and the other of $R_{C1}$ and —$R_{C2}$ is H, where L is of formula:

wherein $n_1$ is 1 or 2, and wherein $R_L$ is selected from optionally substituted $C_{5-20}$ aryl; and $R_N$ is hydrogen.

2. A method according to claim 1, wherein there is a double bond present between the third and fourth positions of the compound.

3. A method according to claim 1, wherein the fused benzene ring is unsubstituted.

4. A method according to claim 1, wherein $n_1$ is 1.

5. A method of potentiating tumour cells for treatment with ionising radiation or chemotherapeutic agents comprising administering to said cells a compound of formula:

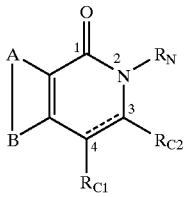

or an isomer, salt, solvate, chemically protected form, or prodrug thereof, wherein:

A and B together represent a fused benzene ring which is optionally substituted with one or more substituents selected from the group consisting of halo, nitro, hydroxy, ether, thiol, thioether, amino, $C_{1-7}$ alkyl, $C_{3-20}$ heterocyclyl, and $C_{5-20}$ aryl; wherein one or more of the substituents may together form a ring;

the dotted line between the 3 and 4 positions indicates the optional presence of a double bond;

one of $R_{C1}$ and $R_{C2}$ is represented by -L-$R_L$, and the other of $R_{C1}$ and —$R_{C2}$ is H, where L is of formula:

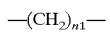

wherein $n_1$ is 1 or 2, and wherein $R_L$ is selected from optionally substituted $C_{5-20}$ aryl; and $R_N$ is hydrogen.

6. A compound of the formula:

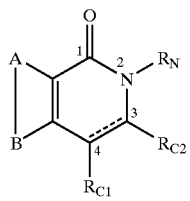

or an isomer, salt, solvate, chemically protected form, or prodrug thereof, wherein:

A and B together represent an optionally substituted, fused aromatic ring;

the dotted line between the 3 and 4 positions indicates the optional presence of a double bond;

one of $R_{C1}$ and $R_{C2}$ is —$CH_2$—$R_L$, and the other of $R_{C1}$ and $R_{C2}$ is H;

$R_L$ is optionally substituted fluoro-phenyl; and $R_N$ is hydrogen.

7. A compound according to claim 6, wherein the fused aromatic ring(s) represented by -A-B- consists of solely carbon ring atoms.

8. A compound according to claim 7, wherein the fused aromatic ring represented by -A-B- is benzene.

9. A compound according to claim 8, wherein the fused aromatic ring is unsubstituted.

10. A pharmaceutical composition comprising compound of the formula:

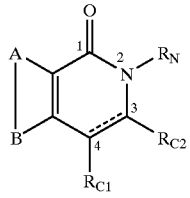

or an isomer, salt, solvate, chemically protected form, and or prodrug thereof, wherein:

A and B together represent an optionally substituted, fused aromatic ring;

the dotted line between the 3 and 4 positions indicates the optional presence of a double bond;

one of $R_{C1}$ and $R_{C2}$ is —$CH_2$—$R_L$, and the other of $R_{C1}$ and $R_{C2}$ is H;

$R_L$ is optionally substituted phenyl; and $R_N$ is hydrogen;

and a pharmaceutically acceptable carrier or diluent.

* * * * *